(12) United States Patent
Graichen et al.

(10) Patent No.: US 9,859,105 B2
(45) Date of Patent: Jan. 2, 2018

(54) MULTIPLE ION GATE METHOD AND APPARATUS

(71) Applicants: Adam Michael Graichen, New Salem, MA (US); Robert H Jackson, Littleton, MA (US); Mark A Osgood, Brookline, NH (US); Ching Wu, Boxborough, MA (US); Jianglin Wu, Acton, MA (US)

(72) Inventors: Adam Michael Graichen, New Salem, MA (US); Robert H Jackson, Littleton, MA (US); Mark A Osgood, Brookline, NH (US); Ching Wu, Boxborough, MA (US); Jianglin Wu, Acton, MA (US)

(73) Assignee: Excellims Corporation, Acton, MA (US)

( * ) Notice: Subject to any disclaimer, the term of this patent is extended or adjusted under 35 U.S.C. 154(b) by 0 days.

(21) Appl. No.: 14/742,653

(22) Filed: Jun. 17, 2015

(65) Prior Publication Data

US 2016/0005581 A1   Jan. 7, 2016

Related U.S. Application Data

(60) Continuation-in-part of application No. 14/338,250, filed on Jul. 22, 2014, now Pat. No. 9,142,395, which is a continuation of application No. 13/792,043, filed on Mar. 9, 2013, now Pat. No. 8,785,848, and a continuation-in-part of application No. 11/776,392, filed on Jul. 11, 2007, now abandoned, application No. 14/742,653, which is a continuation-in-part of application No. 14/703,868, filed on May 4, 2015, which is a continuation of application No. 12/764,808, filed on Apr. 21, 2010, now Pat. No. 9,024,255, application No. 14/742,653, which is a continuation-in-part of application No. 13/602,185, filed on Sep. 2, 2012, now Pat. No. 9,523,657, which is a division of application No. 11/946,679, filed on Nov. 28, 2007, now Pat. No. 7,943,901, and a
(Continued)

(51) Int. Cl.
*H01J 49/00* (2006.01)
*G01N 27/62* (2006.01)
*G01N 30/72* (2006.01)

(52) U.S. Cl.
CPC ........ *H01J 49/0031* (2013.01); *G01N 27/622* (2013.01); *H01J 49/004* (2013.01); *G01N 30/7233* (2013.01)

(58) Field of Classification Search
CPC .... H01J 49/0031; H01J 49/004; H01J 49/009; H01J 49/061; G01N 27/622
See application file for complete search history.

(56) References Cited

U.S. PATENT DOCUMENTS

| | | | | |
|---|---|---|---|---|
| 4,633,083 A | * | 12/1986 | Knorr | G01N 27/622 250/282 |
| 8,173,959 B1 | * | 5/2012 | Boumsellek | G01N 27/622 250/281 |

(Continued)

*Primary Examiner* — Wyatt Stoffa

(57) ABSTRACT

A second gate in an Ion Mobility Spectrometer is used to select or block different time windows of the ion mobility spectrum. A second gate in the Ion Mobility Mass Spectrometer is used to modulate peak intensities in the IMS spectrum, allowing each peak in the IMS spectrum to be unambiguously matched with its set of fragment ions in a subsequent MS-MS mass spectrum.

21 Claims, 16 Drawing Sheets

Related U.S. Application Data continuation-in-part of application No. 13/083,128, filed on Apr. 8, 2011, now Pat. No. 8,314,383, and a continuation-in-part of application No. 12/723,439, filed on Mar. 12, 2010, now Pat. No. 8,258,468, which is a continuation of application No. 11/674,646, filed on Feb. 13, 2007, now Pat. No. 7,705,296, application No. 14/742,653, which is a continuation-in-part of application No. 13/651,837, filed on Oct. 15, 2012, now Pat. No. 9,257,269, which is a division of application No. 11/776,392, filed on Jul. 11, 2007, now abandoned, said application No. 13/083,128 is a division of application No. 11/946,679, filed on Nov. 28, 2007, now Pat. No. 7,943,901.

(60) Provisional application No. 61/609,297, filed on Mar. 10, 2012, provisional application No. 61/171,447, filed on Apr. 21, 2009, provisional application No. 60/867,400, filed on Nov. 28, 2006, provisional application No. 60/766,825, filed on Feb. 14, 2006, provisional application No. 60/807,031, filed on Jul. 11, 2006, provisional application No. 60/891,532, filed on Feb. 26, 2007.

(56) References Cited

U.S. PATENT DOCUMENTS

| Patent/Pub No. | Date | Inventor | Classification |
|---|---|---|---|
| 9,269,548 B2* | 2/2016 | Belov | H01J 49/0031 |
| 2007/0158543 A1* | 7/2007 | Clowers | G01N 27/622 250/282 |
| 2008/0179515 A1* | 7/2008 | Sperline | H01J 49/00 250/290 |
| 2008/0185513 A1* | 8/2008 | Belov | H01J 49/0031 250/288 |
| 2008/0230688 A1* | 9/2008 | Bowdler | H01J 49/40 250/282 |
| 2009/0101810 A1* | 4/2009 | McLean | B82Y 30/00 250/282 |
| 2009/0294647 A1* | 12/2009 | Michelmann | G01N 27/622 250/282 |
| 2010/0108879 A1* | 5/2010 | Bateman | G01N 27/622 250/283 |
| 2011/0127417 A1* | 6/2011 | Ibrahim | H01J 49/004 250/282 |
| 2011/0198493 A1* | 8/2011 | Clemmer | G01N 27/622 250/282 |
| 2011/0248160 A1* | 10/2011 | Belov | H01J 49/0031 250/283 |
| 2011/0284734 A1* | 11/2011 | Hoyes | G01N 27/622 250/282 |
| 2011/0291001 A1* | 12/2011 | Hoyes | H01J 49/0081 250/283 |
| 2012/0025070 A1* | 2/2012 | Miller | G01N 27/624 250/287 |
| 2012/0130700 A1* | 5/2012 | Richardson | G01N 27/622 703/12 |
| 2012/0228491 A1* | 9/2012 | Wu | G01N 27/622 250/282 |
| 2012/0261564 A1* | 10/2012 | Belov | H01J 49/0031 250/282 |
| 2012/0326020 A1* | 12/2012 | Ivashin | G01N 27/622 250/282 |
| 2012/0326023 A1* | 12/2012 | Kozole | G01N 27/622 250/282 |
| 2013/0161506 A1* | 6/2013 | Ugarov | G01N 27/62 250/282 |
| 2013/0187037 A1* | 7/2013 | Wu | G01N 27/622 250/282 |
| 2013/0292562 A1* | 11/2013 | Clemmer | G01N 27/622 250/282 |
| 2014/0339417 A1* | 11/2014 | Hendrikse | H01J 49/0031 250/282 |
| 2014/0346339 A1* | 11/2014 | Wu | C07B 63/00 250/282 |
| 2014/0346346 A1* | 11/2014 | Wu | C07B 63/00 250/287 |
| 2015/0069227 A1* | 3/2015 | Wu | G01N 27/622 250/282 |
| 2015/0194296 A1* | 7/2015 | Verenchikov | H01J 49/0027 250/282 |
| 2015/0233866 A1* | 8/2015 | Verenchikov | G01N 27/622 250/282 |
| 2015/0338374 A1* | 11/2015 | Clemmer | G01N 27/622 250/282 |

* cited by examiner

| | Peak 1 | Peak 2 | Peak 3 | Peak 4 | Peak 5 | Peak 6 | Peak 7 | Peak 8 | Peak 9 |
|---|---|---|---|---|---|---|---|---|---|
| Waveform 1 | 1 | 0 | 1 | ¼ | ½ | ¾ | 1 | 1 | 1 |
| Waveform 2 | 0 | 1 | 1 | 1 | 1 | 1 | ¼ | ½ | ¾ |
| Ratio | ∞ | 0 | 1 | ¼ | ½ | ¾ | 4 | 2 | 1⅓ |

MULTIPLE ION GATE METHOD AND APPARATUS

CROSS-REFERENCE TO RELATED APPLICATIONS

The present application is a continuation in part of U.S. patent application Ser. No. 14/338,250, filed on Jul. 22, 2014, which is a continuation of U.S. patent application Ser. No. 13/792,043, filed on Mar. 9, 2013, now issued as U.S. Pat. No. 8,785,848. Application Ser. No. 13/792,043 claims the benefit of and priority to corresponding U.S. Provisional Patent Application No. 61/609,297, filed on Mar. 10, 2012. Application Ser. No. 14/338,250 is also a continuation in part of U.S. patent application Ser. No. 11/776,392, filed on Jul. 11, 2007, now abandoned.

The present application is a continuation in part of U.S. patent application Ser. No. 14/703,868, filed on May 4, 2015, which is a continuation of U.S. patent application Ser. No. 12/764,808, filed on Apr. 21, 2010, now issued as U.S. Pat. No. 9,024,255. Application Ser. No. 12/764,808 claims the benefit of and priority to corresponding U.S. Provisional Patent Application No. 61/171,447, filed on Apr. 21, 2009.

The present application is a continuation in part of U.S. patent application Ser. No. 13/602,185, filed on Sep. 2, 2012, which is a division of application Ser. No. 11/946,679, filed Nov. 28, 2007, now issued as U.S. Pat. No. 7,943,901. Application Ser. No. 11/946,679 claims the benefit of and priority to corresponding U.S. Provisional Patent Application 60/867,400 filed Nov. 28, 2006. Application Ser. No. 13/602,185 is also a continuation in part of U.S. patent application Ser. No. 13/083,128, filed Apr. 8, 2011, now issued as U.S. Pat. No. 8,314,383. Application Ser. No. 13/083,128 is a division of U.S. patent application Ser. No. 11/946,679, filed Nov. 28, 2007, now issued as U.S. Pat. No. 7,943,901. Application Ser. No. 13/602,185 is also a continuation in part of U.S. patent application Ser. No. 12/723,439, filed Mar. 12, 2010, now issued as U.S. Pat. No. 8,258,468. Application Ser. No. 12/723,439 is a continuation of U.S. patent application Ser. No. 11/674,646, filed Feb. 13, 2007, now issued as U.S. Pat. No. 7,705,296. Application Ser. No. 11/674,646 claims the benefit of and priority to corresponding U.S. Provisional Patent Application No. 60/766,825, filed Feb. 14, 2006.

The present application is a continuation in part of U.S. patent application Ser. No. 13/651,837, filed on Oct. 15, 2012, which is a division of application Ser. No. 11/776,392, filed Jul. 11, 2007, now abandoned. Application Ser. No. 11/776,392 claims the benefit of and priority to corresponding U.S. Provisional Patent Application Nos. 60/807,031 and 60/891,532, filed Jul. 11, 2006 and Feb. 26, 2007 respectively.

The entire contents of all of the above applications are incorporated herein by reference in their entirety.

BACKGROUND OF THE INVENTION

With the recent development of ion mobility based separation technology, ion mobility mass spectrometers (IMS) have come into common use in analytical laboratories. In the past decade, our research has been focusing on the development of high resolution ion mobility devices, and has demonstrated that IMS resolving power is equivalent or better than that of modern HPLC systems. Because of the orthogonality of mobility based separation to HPLC and mass spectrometry (MS), IMS enhances the capability of MS systems for the analysis of complex samples.

Multi-dimensional data from combinations of ion mobility spectrometry (IMS) with mass spectrometry (MS) are powerful for analysis of complex mixtures. Drift tube IMS separations requiring 1-100 ms can be conveniently analyzed by repetitions of 1-100 µs time-of-flight (tof) MS pulses, but combination with the 100-1000 ms cycle times of trapping MS seems problematic: trap style mass analyzers obtain mass-to-charge ratio (m/z) information on a slower timescale than typical signal-averaged mobility experiments. Due to the time consuming nature of ion injection events, dual gate ion mobility devices provide an effective means by which mobility-mass experiments can be accomplished. The inclusion of a two gate system selectively filters ions prior to mass analysis, producing a mobility spectrum by reconstructing sequential windows sampled by scanning the time delay in the opening between the first and second gates. However, this process can be rather lengthy.

SUMMARY OF THE INVENTION

The present invention is a method of operating a dual gate time-of-flight ion mobility spectrometer. Subsequent to separation by mobility in the drift tube, a second ion gate (sometimes referred to as a second gate) is operated with a dynamic waveform comprised of a series of commands that define discrete time periods, or windows, where the gate is open and closed, which permits the selective and concurrent transmission of ions within multiple ion mobility windows (so-called "multi gate" mode). In a further application of multi gate mode, a second ion gate is used to modulate peak intensities in the IMS spectrum, allowing each peak in the IMS spectrum to be unambiguously matched with its set of fragment ions in a subsequent MS-MS mass spectrum.

BRIEF DESCRIPTION OF THE DRAWINGS

The foregoing and other aspects, embodiments, and features of the inventions can be more fully understood from the following description in conjunction with the accompanying drawings. In the drawings like reference characters generally refer to like features and structural elements throughout the various figures. The drawings are not necessarily to scale, emphasis instead being placed upon illustrating the principles of the inventions.

DETAILED DESCRIPTION OF VARIOUS EMBODIMENTS

Figure 1:
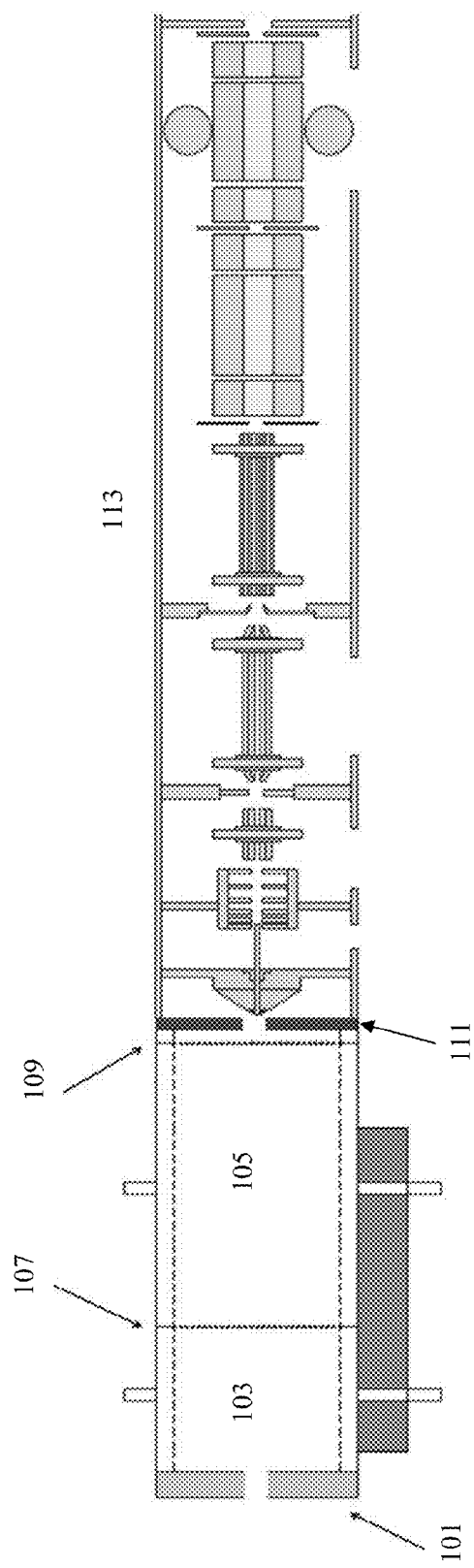
FIG. 1 illustrates a multi gate ion mobility spectrometer-mass spectrometer (IMMS).
Figure 2A:
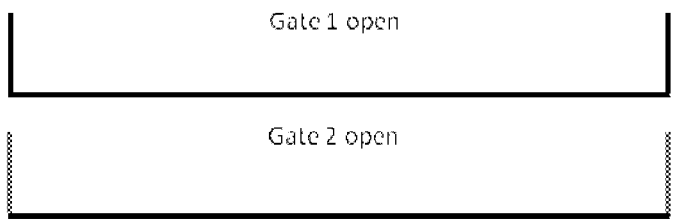
FIGS. 2A, 2B, 2C, and 2D illustrate four modes of operation: Open (FIG. 2A), Single Gate (FIG. 2B), Multi Gate (FIG. 2C), and Scan (FIG. 2D).
Figure 2B:
Figure 2C:
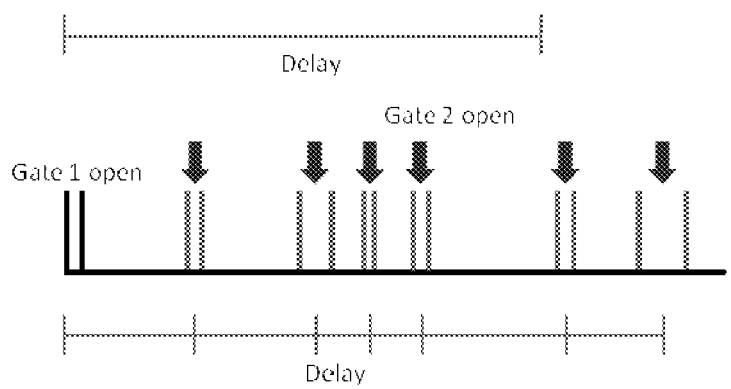
Figure 2D:
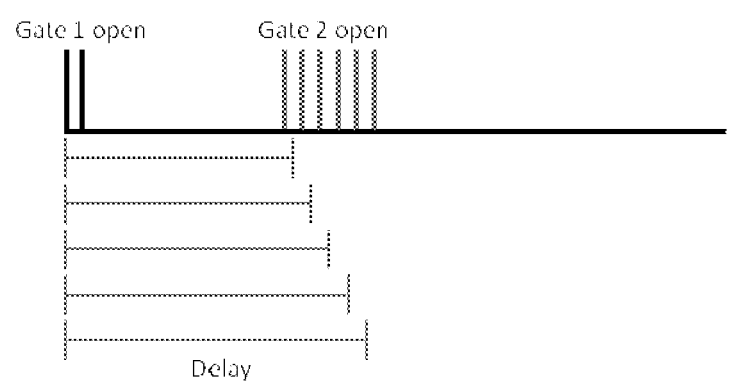

The terms ion mobility separator, and ion mobility spectrometer, and ion mobility based spectrometers are used interchangeably in this invention, often referred to as IMS, including time-of-flight (TOF) IMS, differential mobility spectrometers (DMS), field asymmetric ion mobility spectrometers (FAIMS) and their derived forms. A time of flight ion mobility spectrometer and its derived forms refers to, in its broadest sense, any ion mobility based separation device that characterize ions based on their time of flight over a defined distance. A FAIMS, a DMS, and their derived forms separate ions based on their ion mobility characteristics under high values of normalized electric field.

The systems and methods of the present inventions may make use of "drift tubes." The term "drift tube" is used herein in accordance with the accepted meaning of that term in the field of ion mobility spectrometry. A drift tube is a structure containing a neutral gas through which ions are moved under the influence of an electrical field. It is to be understood that a "drift tube" does not need to be in the form of a tube or cylinder. As understood in the art, a "drift tube" is not limited to the circular or elliptical cross-sections found in a cylinder, but can have any cross-sectional shape including, but not limited to, square, rectangular, circular, elliptical, semi-circular, triangular, etc. In many cases, a drift tube is also referred to the ion transportation and/or ion filter section of a FAIMS or DMS device.

Neutral gas is often referred to as a carrier gas, drift gas, buffer gas, etc. and these terms are considered interchangeable herein. The gas is at a pressure such that the mean free path of the ion, or ions, of interest is less than the dimensions of the drift tube. That is, the gas pressure is chosen for viscous flow. Under conditions of viscous flow of a gas in a channel, conditions are such that the mean free path is very small compared with the transverse dimensions of the channel. At these pressures the flow characteristics are determined mainly by collisions between the gas molecules, i.e. the viscosity of the gas. The flow may be laminar or turbulent. It is preferred that the pressure in the drift tube is high enough that between collisions ions will travel a negligible distance, relative to the longitudinal length of the drift tube, therefore a steady-state ion mobility is achieved.

The phrase "and/or," as used herein in the specification and in the claims, should be understood to mean "either or both" of the elements so conjoined, i.e., elements that are conjunctively present in some cases and disjunctively present in other cases.

Unless otherwise specified in this document the term "particle" is intended to mean chemical and/or biological single or plurality of sub-atomic particle, atom, molecule, large or macro molecule, nanoparticle, or other matters that are vapor, droplets, aerosol, liquid, solid that follow a mobile medium, where the medium can be a gas, a liquid, supercritical fluid and/or other fluidic materials.

The present invention is a method of operating a dual gate time-of-flight ion mobility spectrometer. Subsequent to separation by mobility in the drift tube, a second ion gate (sometimes referred to as a second gate) is operated with a dynamic waveform comprised of a series of commands that define discrete time periods, or windows, where the gate is open and closed, which permits the selective and concurrent transmission of ions within multiple ion mobility windows (so-called "multi gate" mode). The ion gate construction can be a Bradbury Nielson ion gate or any other known art of ion gate construction for an ion mobility spectrometer. In many case, the ion gate can be constructed to achieve the purpose of blocking or deflecting ions from moving in its ordinary path. In some cases, the voltage applied to a deflector, which can prevent ions from moving forward, could be considered as an ion gate, as long as the opening and closing is quick enough: an ion gate for an ion mobility spectrometer requires a clean "on-off" of the ion beam in order to allow adjacent peaks in an mobility spectrum to be passed or blocked by the ion gate.

A prior art time of flight ion mobility spectrometer operates in a manner either only having one ion gate or using a second gate to select ions with one mobility (represented by a drift time of a peak in the ion mobility spectrum) to be detected on a Faraday detector: the ion mobility analyzer is use to monitor the signal intensity of a single ion of interest. In some operations, the moving second gate method is used to sequentially allow ions with different drift time to reach the ion detector; therefore, an ion mobility spectrum can be constructed. The present invention describes a novel ion mobility operational method: for each opening of the first ion gate, the second ion gate opens for multiple times to allow selected ion mobility separated ions to be recorded either at a Faraday detector or a mass spectrometer. In the case of using a mass spectrometer, the Faraday detector is a "pass through" Faraday detector that allows a portion of the ions to pass through the detector and enter the mass spectrometer for further mass analysis.

In one embodiment, present invention describes a method for operating a ion mobility spectrometer, by opening a first ion gate (normally positioned in the vicinity close to the ionization source) to allow a packet of mixed ions into the ion mobility analyzer; the ions that are allowed to enter the ion mobility analyzer will be separated while they travel through the ion mobility analyzer (for a time of flight ion mobility spectrometer, the analyzer is a drift tube; for a FAIMS the analyzer is an ion filter). This method further includes opening a second gate (that is positioned in the vicinity close to the ion detector end of the analyzer) multiple times according to a waveform consisting of a series of time windows to allow ions with certain ion mobilities (drift times) to pass through the second gate and block the ions with other ion mobilities (drift times). In some cases, the series of time windows may be predetermined based on a previous offline measurement of the sample mixture, or offline measurements of analytical standards. Alternatively, the series of time windows may be predetermined based on drift times predicted from known mobility or collision cross-section values, or theoretical calculations of ion mobility or collision cross-section. In other cases, the waveform could be generated "online" based on a measurement of the sample itself, either at the Faraday detector or at the mass spectrometer, followed by rapidly determining the time windows that correspond to the components of the sample being analyzed. In many cases, the Faraday detector signal can be measured first, and that information can be used to generate a waveform of time windows that only passes the ions of interest to the mass spectrometer for mass analysis. This operation can be considered as a method using on-line ion mobility measurement of the mixed ions.

Because the ion mobility (and drift time) has a direct relationship with the collision cross section of ions, the IMS can be configured in such a way where the second gate will selectively pass ions with certain collision cross sections. The ions with certain ion mobilities are the ions of interest; the series of time windows is chosen to select ions with certain collision cross section from the mixed ions.

In one embodiment, the time windows when the second gate is closed are chosen to selectively block ions with specific ion mobilities. In this case, the second gate can be open for most of the time, allowing a majority of the ions to pass, and closed for a period of time that will block the undesired ions (with certain drift time, certain ion mobility, and/or certain collision cross section). In this case, if there is a mass spectrometer after the second ion gate, the selectively blocked ions are prevented from entering into the mass spectrometer for mass analysis. In practical operation, eliminating unwanted ions for a mass spectrometer can improve the performance of the mass spectrometer for those ions of interest; as an example, it could reduce space charge effects, and it could increase mass accuracy.

The method for operating a ion mobility spectrometer may also include generating two or more waveforms, wherein the two or more waveforms have different combinations of opening times and widths; opening and closing the second ion gate according to the first waveform, while collecting a spectrum; opening and closing the second ion gate according to the second and subsequent waveforms, while collecting additional spectra; comparing the two or more spectra.

In a variety of embodiments, the waveform of the second gate can be used as an encoding method to link the ion mobility and mass analysis. As a non-limiting example, the second gate can be opened for one half of the width of an ion mobility peak, therefore only half of the ions with this ion mobility (drift time) can contribute to the peak in a mass spectrum; by linking the intensity or peak area changes in an ion mobility spectrum and a mass spectrum with known second gate operation, a ion mobility peak can be associated to an ion mass (m/z) peak.

The method for operating a ion mobility spectrometer may include detecting a first ion mobility spectrum from a sample; generating two waveforms based on the ion mobility spectrum, wherein the two waveforms have different combinations of notch sizes for each peak; opening and closing the second ion gate according to the first waveform, while collecting fragment ion data in the mass spectrometer; opening and closing the second ion gate according to the second waveform, while collecting fragment ion data in the mass spectrometer; comparing the two fragment ion mass spectra, and matching each fragment ion with its peak in the first IMS spectrum based on the ratios of the fragment peak intensities. In one case, the first ion mobility spectrum is detected using a Faraday plate; in another case, the first ion mobility spectrum is detected using the mass spectrometer.

In one embodiment, a ion mobility spectrometer includes a first ion gate to allow a packet of mixed ions into an ion mobility analyzer to separate ions, and a second ion gate; for each opening of the first gate, the second gate opens multiple times at a series of time windows to allow ions with certain ion mobilities to pass through the second gate and block the ions with other ion mobilities. The opening and closing of the first and the second ion gate are controlled using instrument control electronics and computer software. The ion mobility spectrometer that has two ion gates may have a Faraday detector; such Faraday detector may be a pass through Faraday detector that allows a portion of the ions to be detected and the other portion to pass through. The ions that pass through the Faraday detector may enter into a mass spectrometer.

In one embodiment, the Faraday detector may be placed at a location that is before the second gate; or the Faraday detector may be placed after the second gate. When using a mass spectrometer behind the second ion gate, the Faraday detector may or may not be included in the configuration. In cases where a pass through Faraday detector is included, the Faraday signal can be used to perform data dependent ion mobility-mass measurements. In the case where the second gate is behind the Faraday detector, the second ion gate can be part of the mass spectrometer inlet, either at the ambient pressure side or in the vacuum side. The ion gate construction is not limited to a Bradbury-Nielson gate construction. In a variety of embodiments, the second gate can be a segmented ion gate that passes ions with different mobility in different regions of the ion gate; the ions that pass through the ion gate can be detected using a Faraday detector or pass into a mass spectrometer. Multiple inlets for a mass spectrometer may be constructed to receive ions with different ion mobility.

One embodiment of the dual gate time-of flight ion mobility spectrometer is shown schematically in FIG. 1. The IMS is shown coupled to a mass spectrometer 113, but for some applications the mass spectrometer can be omitted. The IMS includes an interface region 101 after an ion source (not shown), a desolvation region 103, and a drift region 105. The drift region is also referred to as a drift tube. A first ion gate 107 is located at the start of the drift tube, and a second ion gate 109 is located after the drift tube. An optional Faraday detector 111 is shown here after the second ion gate. The Faraday detector is also referred to as a Faraday plate. Alternatively, the Faraday detector can be located before the second ion gate, or the Faraday detector can be omitted. The Faraday detector is shown as a "pass through" type, which can pass ions into the MS through an opening in the center, while detecting ions incident on the periphery to produce an IMS spectrum.

Previous dual gate IMS systems suffer from a reduction in experiment speed in order to perform mobility scanning to identify the drift times of ion populations, limiting the widespread adaptability of these devices. A further challenge emerges when prior separation based on High Performance Liquid Chromatography (HPLC) is desired. Even high quality HPLC separations may not fully resolve each component and be too complicated to obtain all of the desired information in one acquisition. Unlike these previous dual gate systems, our device can be readily united with HPLC instrumentation. This capability is made possible by the implementation of our data dependent gating waveforms. As co-eluting components may further separate in the IMS dimension, previous dual gate Ion Mobility-Mass Spectrometer (IMMS) instruments would only allow one of these peaks to be investigated at a time in the mass spectrometer (for example, by MS/MS) if the drift time was previously established. Since most HPLC separated species have transient elution profiles, this would severely restrict the number of IMS peaks that could be sampled while the analyte was eluting from the column. Our multiplexing approach is of particular significance as the multi gate waveforms enable multiple IMS peaks (from one previous LC peak) to be concomitantly interrogated by performing tandem mass spectrometry within the same LC experiment, without loss of the precursor-product relationship. The optional Faraday detector functions to (A) identify peaks for notch location in generating the gating waveforms and (B) monitor the ion signal at each of these drift times throughout the period of time for which both gating waveforms are applied, in order to correct for any fluctuation in available ion intensity between waveform 1 and 2 due to changes in the elution profile of the LC peak.

Software recognizes a predetermined number of ions present above a certain intensity threshold in the IMS spectrum (from the Faraday detector), communicates the drift times/widths of detected peaks (from the Faraday detector) to the appropriate controls that define and generate the multi gate notched waveforms, calculates the expected intensity ratios based upon the information from the IMS spectrum and notching patterns chosen, monitors the IMS spectrum as ions are passed into the MS, corrects expected intensity ratios if IMS peak intensity changes during time in which waveform 1 and 2 are applied/MS data collected, and can generate a ratiogram or table from the MS results obtained from waveform 1 and 2.

A multi gate waveform generator can use input from the Faraday plate detector and software to direct the location of notches in the waveforms.

The mass spectrometer needs to be capable of non-mass selective fragmentation of the entire mass range ("All-Ion Fragmentation" or AIF). This includes many types of commercially available mass spectrometers.

An example application of "Multi Gate" mode is for pharmaceutical reaction monitoring, which involves simultaneous monitoring of the starting, intermediate, and product materials. In particular, the ability to distinguish the fragments from the intermediate materials can provide additional information about the reaction mechanism.

Adding a "Multi Gate" IMS in front of a mass spectrometer that does not have mass selective fragmentation will allow that mass spectrometer to perform Selected Reaction Monitoring (SRM), Multiple Reaction Monitoring (MRM), and Parallel Reaction Monitoring (PRM) experiments. Mass spectrometers that do not have mass selective fragmentation generally include scan-type instrumentation such as triple quadrupole mass spectrometers.

Traditional trap-type mass spectrometers can monitor one transition pair (SRM), but it is a slow process; a precursor-ion isolation, fragmentation, product-ion storage, and acquisition must be done for each transition pair.

For mass spectrometers that already have the capability for mass selective fragmentation, addition of a front end "Multi Gate" IMS will allow enhanced detection confidence in SRM/MRM-style experiments, increased number of precursor ions screened, and possibly multiplexed MS/MS for non database compounds. Multi gate IMS can enhance the Parallel Reaction Monitoring (PRM) ability as a result of (A) increased specificity due to mobility filtering resulting in an added layer of confidence for peptide identity confirmation, and (B) a greater number of precursor ions monitored during a particular scan as multiple mobility targeted ions could be transferred instead of just one mass targeted ion in a stepwise manner. Additionally, multi gate IMS could provide encoding for non-peptide ions (not in databases) using the method proposed above.

In applications involving identifying unknowns, mobility selection with a multiplexed IMS approach utilizing a multi gate mode may give better specificity than mass selection alone, due to ions having the appropriate combination of drift time and accurate m/z (versus just accurate m/z) at the MS level, or the appropriate combination of drift time and accurate fragment m/z (versus just accurate fragment m/z) at the MS/MS level. Examples for usage could be any time SRM/MRM or PRM experiments are utilized.

One must remember to look at the tolerance of the quadrupole, which may transmit a small range of m/z. The problem of interfering or isobaric ions in SRM analysis has been alleviated with the use of differential mobility separation (DMS/FAIMS). Although this has been shown to lower the limit of detection (LOD) and increase the dynamic range, it also increases the duty cycle and therefore reduces the number of analytes that can be measured concomitantly in a complex sample. Again, a multiplexed IMS approach utilizing a multi gate mode would be beneficial.

A multi gate mode could be used to monitor multiple drift windows, all corresponding to one compound (for example, a protein within a complex mixture), thereby assuring that one is indeed detecting the analyte of interest. If present, multiple charge states would pass and be detected, aiding confidence in identification.

In mass spectrometer models where ions cannot be specifically isolated for fragmentation, our multi gate IMS device would allow selective removal of components for cleaner MS/MS, as well as reducing the complexity of the computational and data interpretation tasks when co-fragmentation of multiple peptides occurs. In all-ion fragmentation (AIF), data is acquired alternating between MS scans and AIF scans at high resolution (~100,000). An elution profile of each fragment, along with each precursor is collected. To assign a precursor-product ion correlation, the elution profiles must match precisely. Multiple precursor ions may be fragmented simultaneously during data acquisition, however, based on the principle of time-alignment correlation, a particular set of product ions can be grouped or deconvoluted to the composite mass spectra. This approach still suffers from the analysis of complex biological mixtures where exact co-elution of peptides in common. Some prior art has used gas-phase ion mobility separation such that the alignment of precursors and fragments is based also on drift time, allowing up to 60% higher proteome coverage and higher confidence in protein and peptide identifications. The incorporation of IMS, specifically operating in "multi gate" mode, could provide substantial gains in peptide identification with AIF. This is illustrated in FIGS. 12A, 12B, 12C, and 12D, which show a proposed AIF method incorporating IMS selection to eliminate misidentification of fragment ions from simultaneous dissociation of co-eluting (overlapping) LC peaks [shown at four chromatographic elution time points]. In FIGS. 12A, 12B, 12C, and 12D, three theoretical compounds are observed within a narrow LC elution time range. Two of these species show complete co-elution, while the elution profile of the third only partially overlaps. However, all three are resolved by IMS. Alternating the passage of overlapping ions (represented by the first two traces) could be used to generate distinct MS and MS/MS spectra for each compound (A & B). This process would continue for the duration of the elution profile for these compounds or until an additional peak was detected by IMS. As displayed in FIG. 12C, if an additional peak (the third trace) is detected before the previous peaks are finished eluting, this new peak would be included in the alternating passage of the overlapping ions using "multi gate" mode. In this way, multiple ions could be detected over essentially their entire respective chromatographic elution profiles. Traditional data analysis would be sufficient for precursor/product ion correlation without inevitable ambiguous correlation assignments.

In comparison to AIF without prior IMS separation, FIGS. 9A, 9B, 9C, and 9D illustrate the uncertainty associated in determining fragment ion origin for co-eluting species: for an AIF method on mass spectrometer models with no IMS selection, product-precursor ion misidentification is unavoidable during co-elution of overlapping LC peaks 901, 903, and 905; these are shown at four chromatographic elution time points in FIGS. 9A, 9B, 9C, and 9D.

In one embodiment, a multiplexing strategy can be done with simultaneous notches of mobility (enabled by "multi gate" operation). This can be a way to collect LC data with no Faraday detector, assigning MS/MS data to IMS windows post acquisition, thereby creating a pseudo-IMS chromatogram. A typical experiment involves the random selection of five out of a 100 possible 4 m/z wide isolation windows in the range of 500-900 m/z to be analyzed together in each multiplexed scan. These are chosen as the instrument loops sequentially through an inclusion list containing a sequence of 4935 previously-defined isolation windows. Each window is isolated, fragmented, and trapped serially in time followed by the collective mass analysis of all 5 windows in the ion trap mass spectrometer. The obtained spectra are then demultiplexed automatically during post-processing. Applying this method by utilizing m/z selection windows followed by mobility selection windows (which may require two LC injections) could potentially allow the user to also piece together a multidimensional IMS-MS plot. Linkage of MS and IMS peak information may be possible through the MS/MS data collected.

Four modes of operation are illustrated schematically in FIGS. 2A, 2B, 2C, and 2D.

In Open Mode (FIG. 2A), ions flow continuously through both ion gates unrestricted into the mass spectrometer. Conventional mass spectral data can be obtained operating in this mode.

In Single Gate Mode (FIG. 2B), ions within a narrow specified ion mobility range can be selected and allowed to pass into the mass spectrometer. All other ions are blocked.

In Multi Gate Mode (FIG. 2C), multiple openings and closings of the second gate allow the selection and concurrent passage of multiple ion mobility windows into the mass spectrometer.

Scan Mode (FIG. 2D) consists of scanning the delay in opening of the second ion gate after the first ion gate has been opened; this is done by sequentially stepping a window of variable drift width across the chosen drift time range. This mode is used if the drift times of analyte species are unknown, or if the user wishes to generate a comprehensive multi-dimensional IMS-MS plot from a complex mixture.

Figure 3:
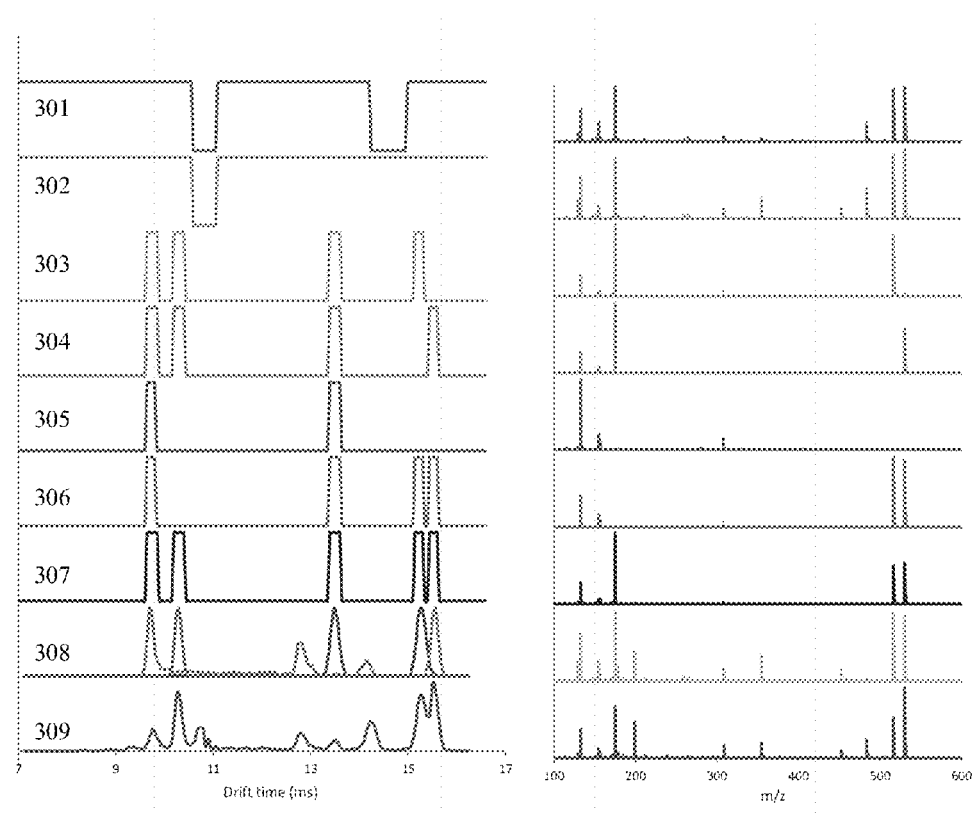
FIG. 3 illustrates multi gate operation for selective ion removal, or selective ion passage, with corresponding ion mobility spectra.

FIG. 3 shows the use of multi gate operation for multiple and simultaneous mobility-based ion transmission. The same sample is used for all spectra in FIG. 3. At the bottom of the FIG. 3, trace 309 shows the ion mobility spectrum on the left, and the mass spectrum on the right, for the sample with the second gate left open. Traces 301 through 307 each show a gate waveform on the left side, and on the right the corresponding mass spectrum when that gate waveform is applied to the second gate using the same sample as shown in 309. For the waveforms shown, the high state is gate open, and the low state is gate closed. Traces 301 and 302 show "reverse notch" waveforms being used for selective ion removal. The mass spectrum for 301 shows removal of background ions at m/z 199 & 453. The mass spectrum for 302 shows removal of background ions at m/z 199 only. Traces 303, 30, 305, 306, and 307 show "regular notch" waveforms being used for selective ion passage.

Figure 4:
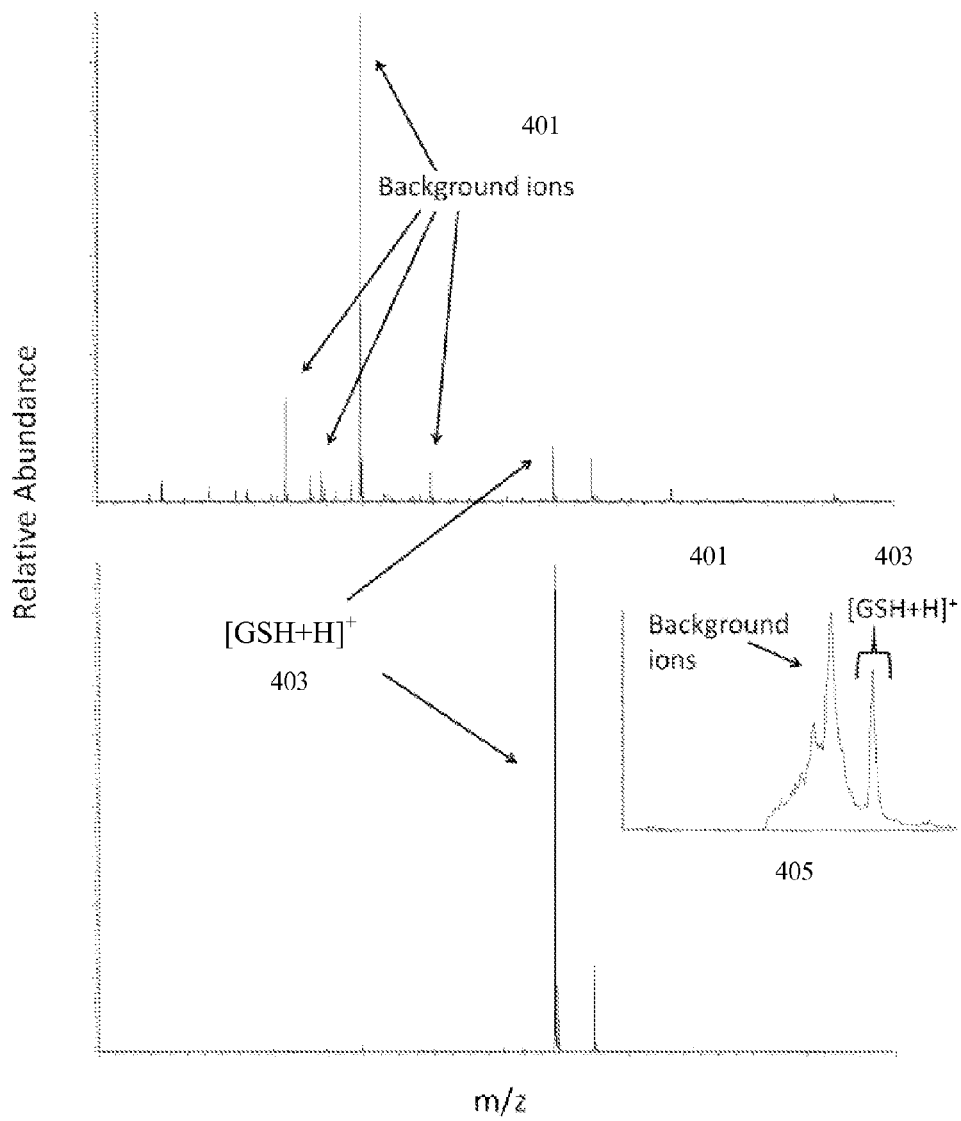
FIG. 4 illustrates use of multi-gating for removal of contaminants.

Multi gating can be used to selectively remove unwanted contaminants, so that the contaminants do not fill the trap. FIG. 4 shows an example of multi gating for removal of contaminants: in the upper trace, unwanted background ions 401 are co-populating the trap with the analyte glutathione (GSH) 403; the lower trace shows a cleaner mass spectrum following removal of background ions by operating in "single gate" mode, for selective accumulation of GSH in the ion trap. The inset 405 displays the initial IMS scan used to identify the drift times of the background ions for exclusion.

Figure 5A:
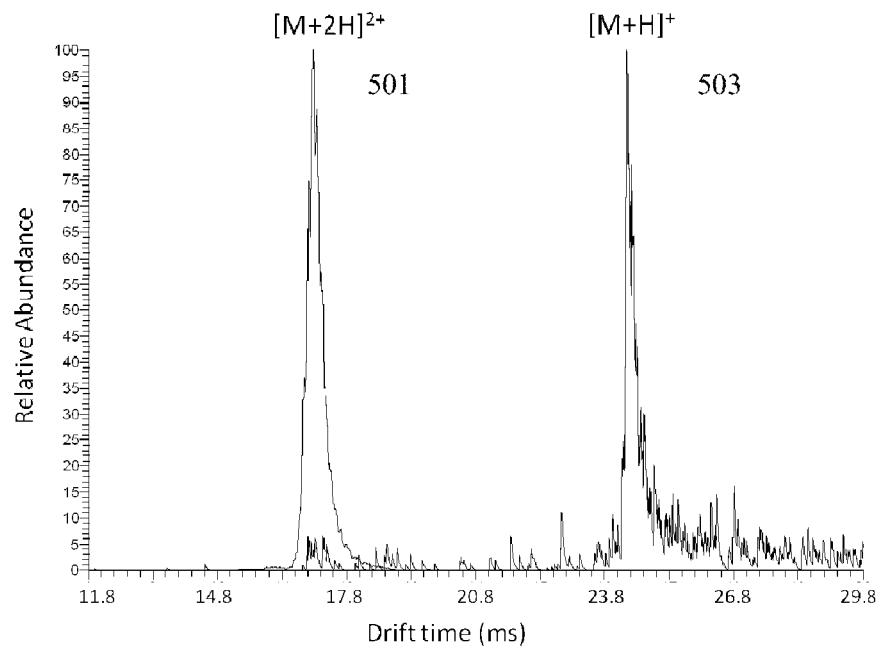
FIGS. 5A and 5B illustrate use of multi-gating for selective charge state enrichment.
Figure 5B:
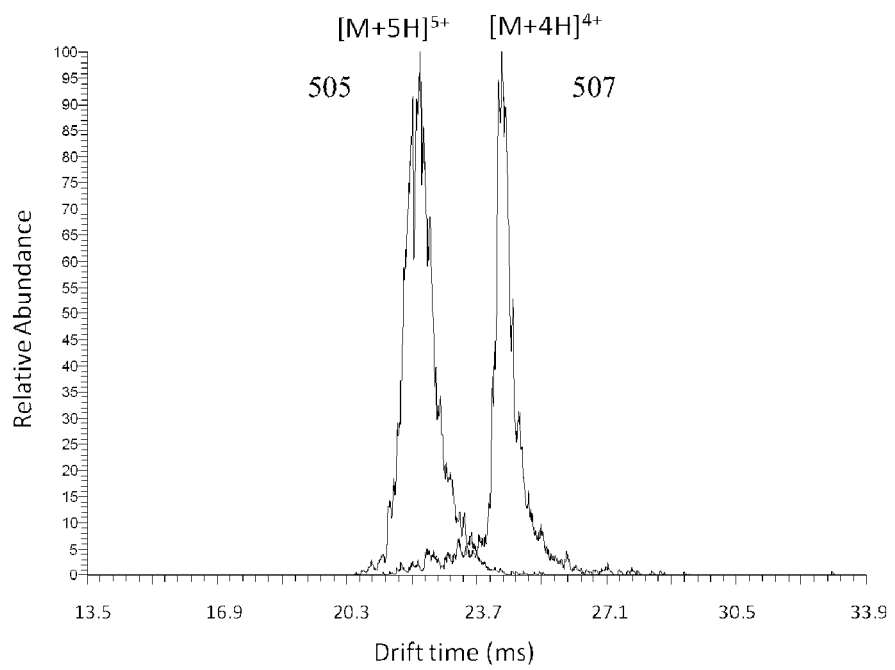

Multi gating can be used for selective charge state enrichment. In some cases, ions of the same analyte with different charge states will fragment differently. Multi gate mode can be used to select two or more charge states that give complementary information, for example, to maximize coverage in sequencing peptides. In FIGS. 5A and 5B, two specific charge states are selectively gated into the mass spectrometer: in FIG. 5A, 1+ and 2+ Bradykinin (503 and 501 respectively), and in FIG. 5B, 4+ and 5+ insulin (507 and 505 respectively).

Figure 6:
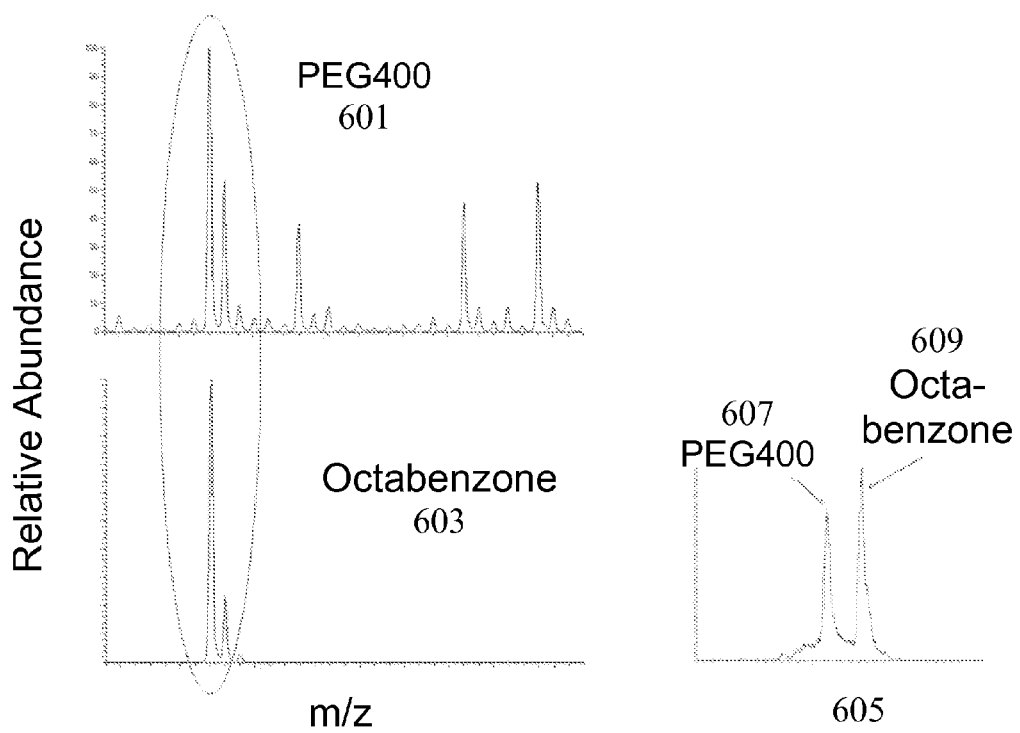
FIG. 6 illustrates use of multi-gating for eliminating isobaric interferences.

Multi gating can be used to eliminate isobaric interferences, that is, ions with the same m/z as the analyte of interest. FIG. 6 (left) shows individual mass spectra of the polyethylene glycol PEG400 (top, 601) and octabenzone (bottom, 603), showing spectral overlap at m/z 327. A reconstructed IMS chromatogram (right, 605) shows the separation of these nominally isobaric species by ion mobility, where the polyethylene glycol PEG400 (607) and octabenzone (609) peaks are well separated. As PEG can be a widely encountered contamination in MS, the presence of this interference at many m/z values may dominate the spectrum and limit the observation of specific analytes of interest. Pre-MS cleanup methods can be implemented to remove salts, detergents, and other interferences, however, such purification procedures are generally time consuming, low throughput, and risk the loss of precious sample.

Figure 7A:
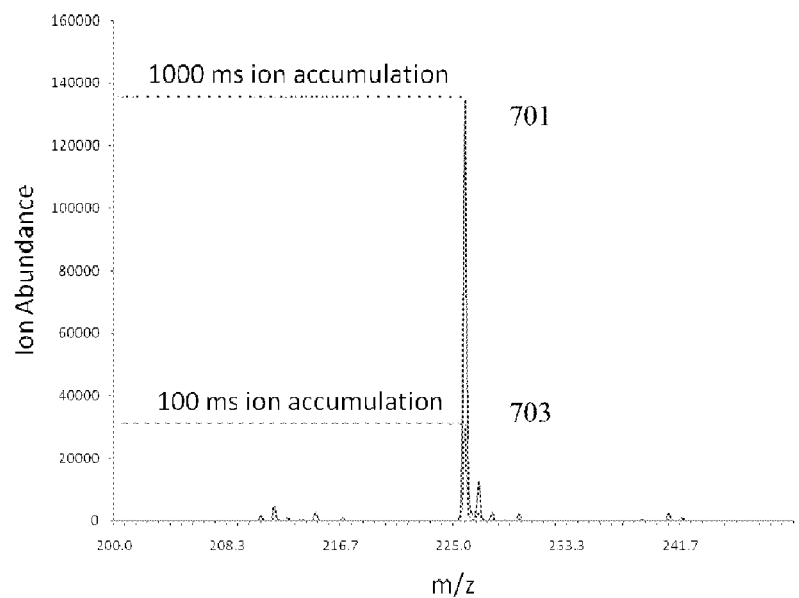
FIGS. 7A and 7B illustrate targeted accumulation and identification confidence.
Figure 7B:
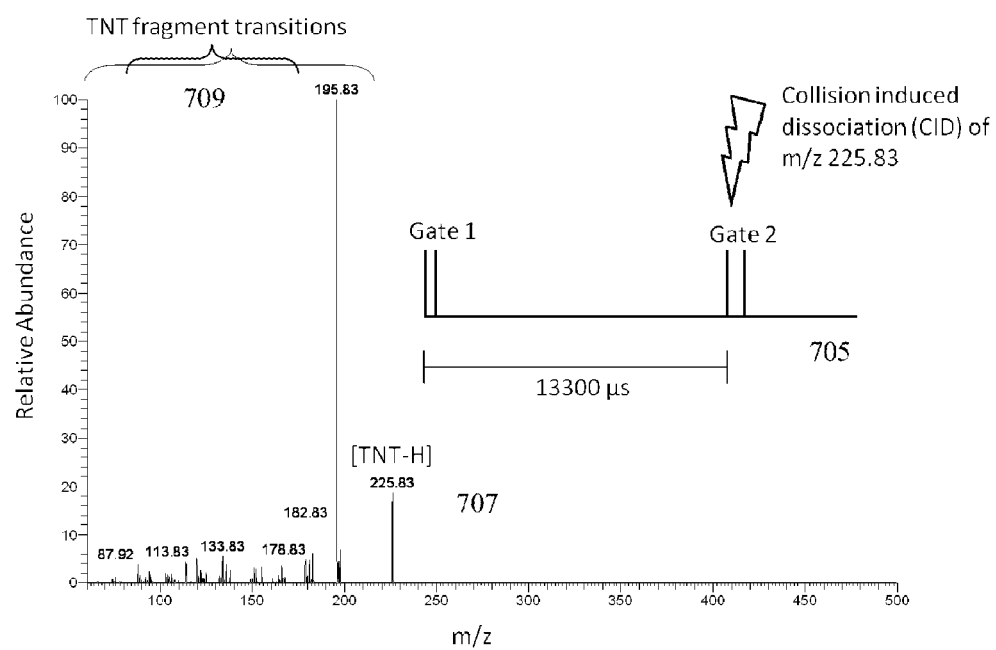

Multi gating allows targeted accumulation and enhanced identification confidence. By selectively removing all background ions, extended ion accumulation times become possible for improved detection sensitivity. Fragmentation of the single clean analyte gives a clean fragment spectrum as well. FIGS. 7A and 7B illustrate this for TNT (trinitrotoluene). FIG. 7A shows ion abundance for a normal 100 ms trap accumulation (703) and for an extended 1000 ms trap accumulation (701); the long accumulation time (1000 ms) still gives a clean mass spectrum for [TNT–H]–. FIG. 7B shows IMS coupled parallel reaction monitoring (PRM) of TNT for highly specific analyte confirmation. The inset 705 shows the Gate 2 pulse that selects only the TNT peak; the mass spectrum shows the TNT precursor ion 707 and the TNT fragments 709 after fragmentation by collision induced dissociation.

Figure 8A:
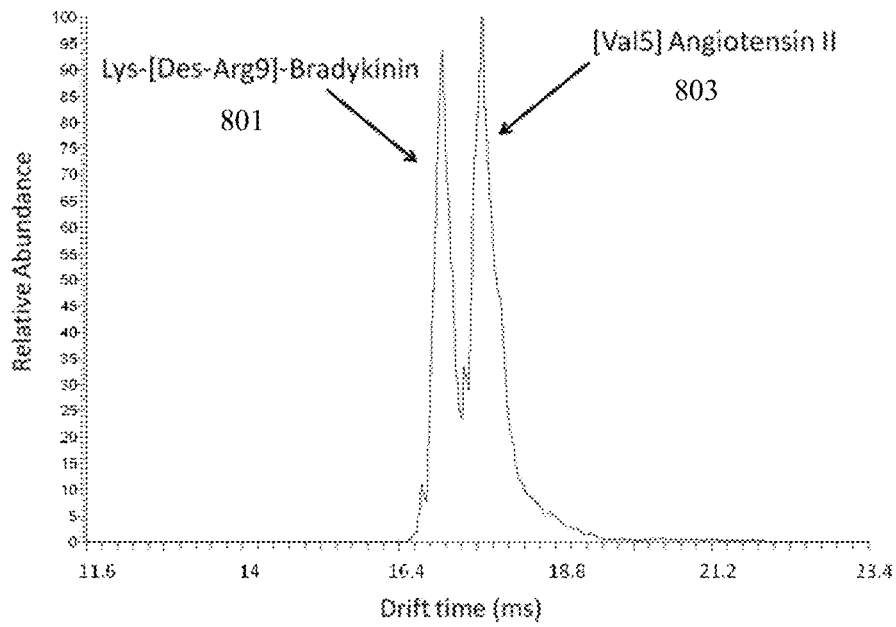
FIGS. 8A and 8B illustrate separation of pseudo-isobaric species.
Figure 8B:
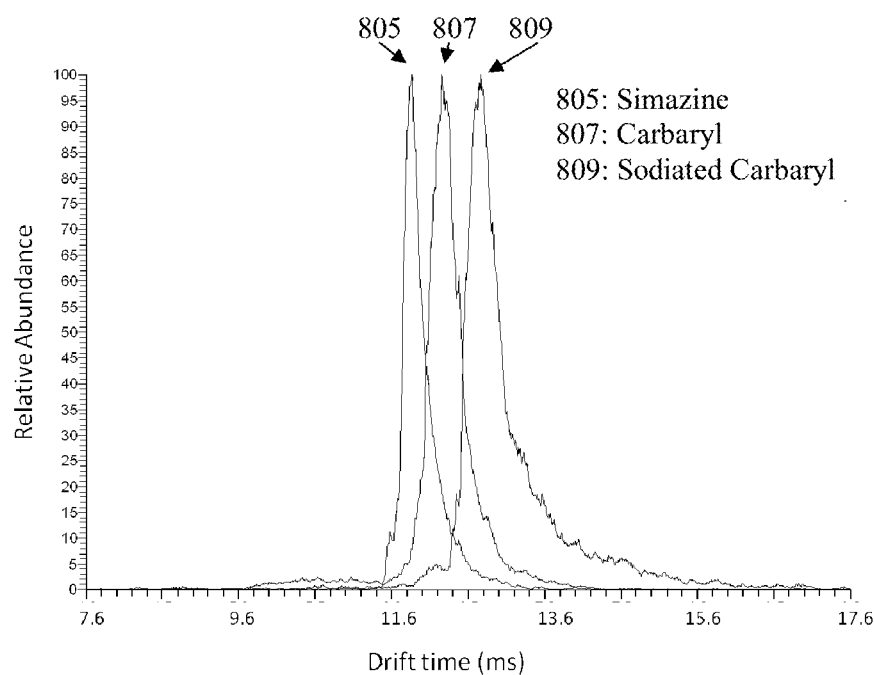
Figures 9A, 9B:
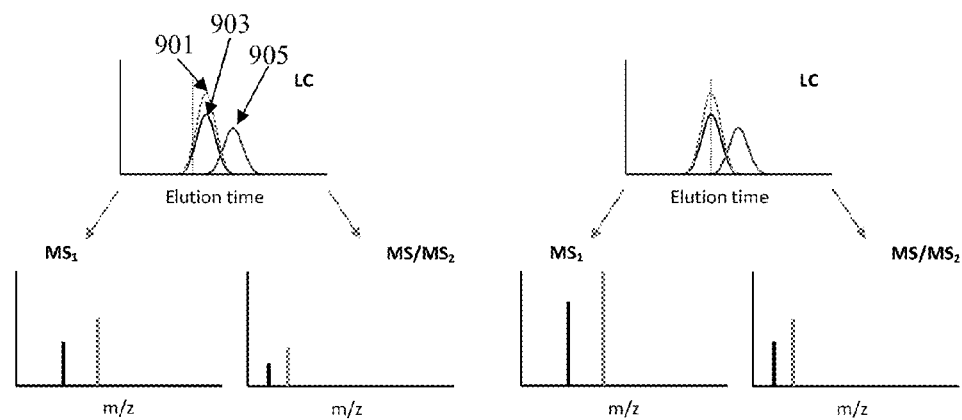
FIGS. 9A, 9B, 9C, and 9D illustrate the uncertainty associated in determining fragment ion origin for co-eluting species, for all-ion fragmentation without prior IMS separation; shown are four chromatographic time points in FIGS. 9A, 9B, 9C, and 9D.
Figures 9C, 9D:
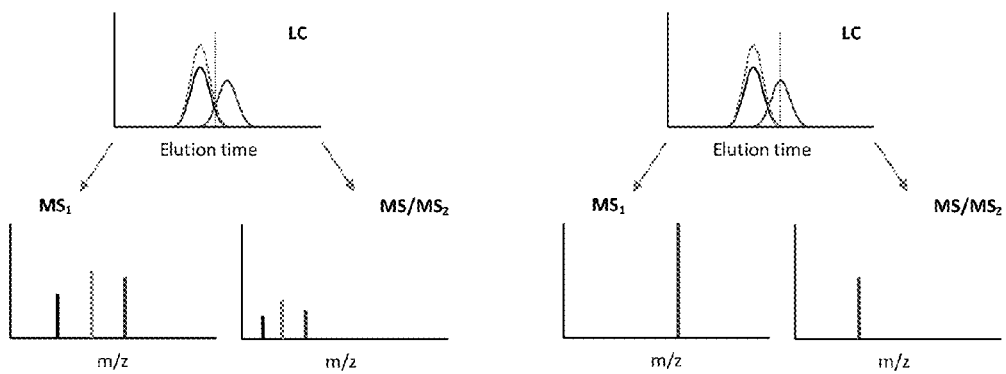

FIGS. 8A and 8B show separation of pseudo-isobaric species using IMS "scan" mode, for Lys-[Des-Arg9]-Bradykinin and [Val5] Angiotensin II (m/z: 517), 801 and 803 respectively in FIG. 8A, and simazine and carbaryl (m/z: 202), in FIG. 8B, where 805 is the simazine peak, and 807 and 809 are carbaryl peaks.

One specific application of the present invention is a multiplexed IMS-MS/MS method that can increase throughput when a dual gate system is used with liquid chromatography (LC) separation, and can facilitate definitive identification of precursor-product relationships for non-database species.

Figures 10A, 10B:
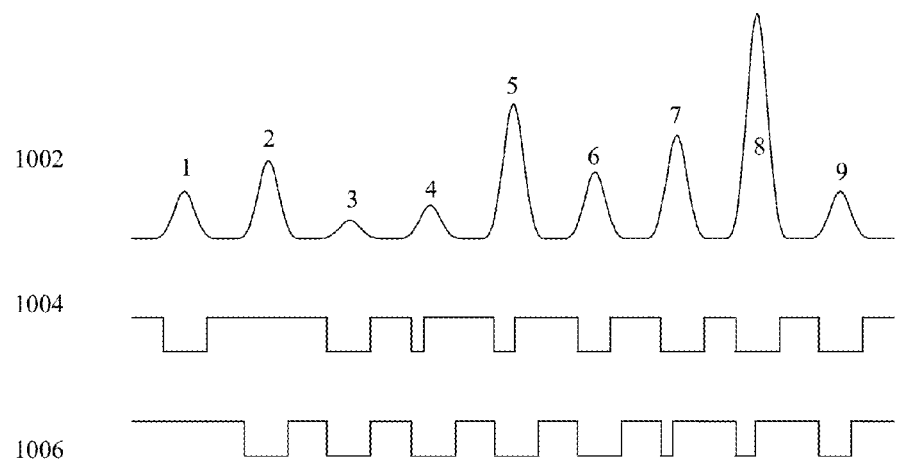
FIG. 10A shows a simulated IMS spectrum of a sample containing 9 compounds, along with two waveforms applied consecutively to Gate 2 in order to simultaneously transfer all ions into the mass spectrometer for co-fragmentation. (For the gate waveforms, low=gate open, and high=gate closed.) The ratio of gated notch widths between waveform 1 and 2 for each ion is distinct, allowing demultiplexing of the MS/MS spectra.
FIG. 10B shows the ion intensity ratios utilized for precursor-product ion correlation with each IMS peak for the example IMS spectrum of FIG. 10A.

This multiplexed method takes advantage of the ability to simultaneously control the width of a second ion gate, and therefore the ion abundance, of multiple ion populations passing into the mass spectrometer. By utilizing a pair of unique and data dependent gating waveforms in sequence, intensity changes for the ions chosen for selective transmission can be induced. These distinct intensity changes can be calculated for each ion, and will also apply to the intensity changes of all corresponding fragment ions formed upon dissociation within the mass spectrometer. Therefore, an encoding scheme is made possible to group or deconvolute particular subsets of product ions to the specific precursor ion from which they originated. To utilize this method, an initial IMS spectrum is first collected by (A) a Faraday cup detector, or (B) by scanning the delay in the opening between the first and second ion gates, thereby sequentially stepping a window of variable drift width across the chosen drift time range for MS detection. The resulting ion mobility spectrum is used to determine both the presence and position of the peaks corresponding to separated ions. FIG. 10A shows a simulated IMS spectrum 1002 of a sample containing 9 compounds, along with Waveform 1 and Waveform 2 (1004 and 1006 respectively) applied consecutively to Gate 2 in order to simultaneously transfer all ions into the mass spectrometer for co-fragmentation. (For the gate waveforms, low=gate open, and high=gate closed.) The ratio of gated notch widths between waveforms 1 and 2 for each ion is distinct, allowing demultiplexing of the MS/MS spectra. FIG. 10B shows the ion intensity ratios utilized for precursor-product ion correlation with each IMS peak for the example IMS spectrum and Gate 2 waveforms of FIG. 10A.

Figure 11:
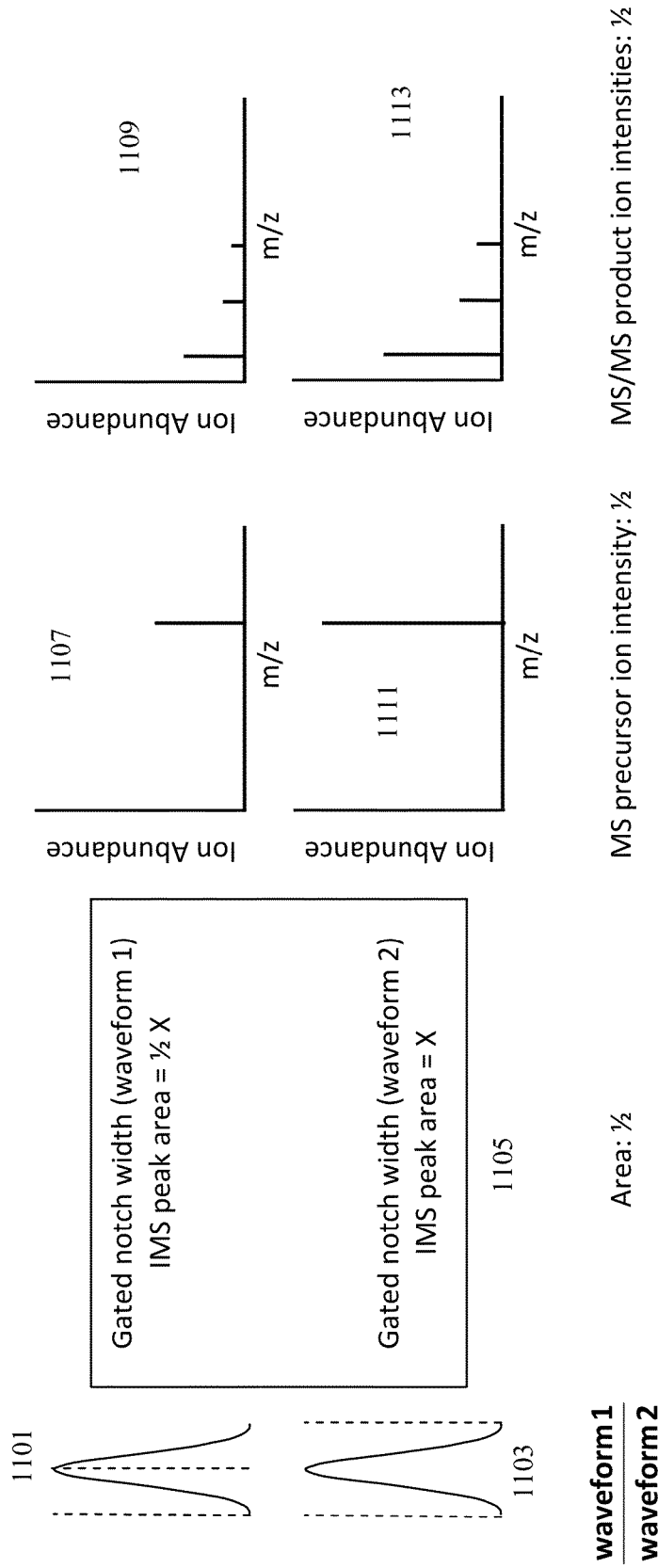
FIG. 11 shows an encoding scheme made possible by ratio comparison of IMS peak area and MS or MS/MS ion intensity due to notch width differences between waveforms, illustrated for Peak 5.
Figure 12A:
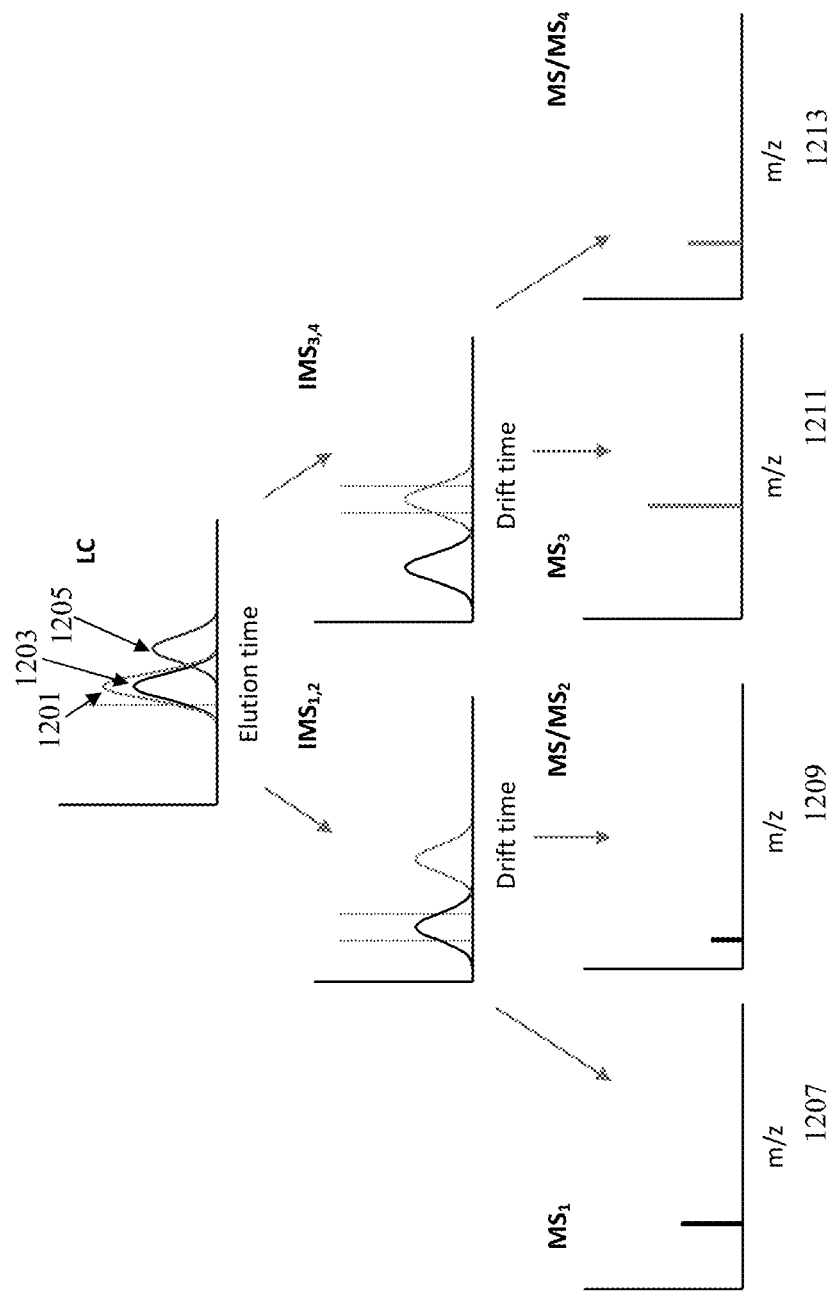
FIGS. 12A, 12B, 12C, and 12D illustrate a proposed all-ion fragmentation method incorporating IMS selection to eliminate misidentification of fragment ions from simultaneous dissociation of co-eluting (overlapping) LC peaks; shown are four chromatographic time points in FIGS. 12A, 12B, 12C, and 12D.
Figure 12B:
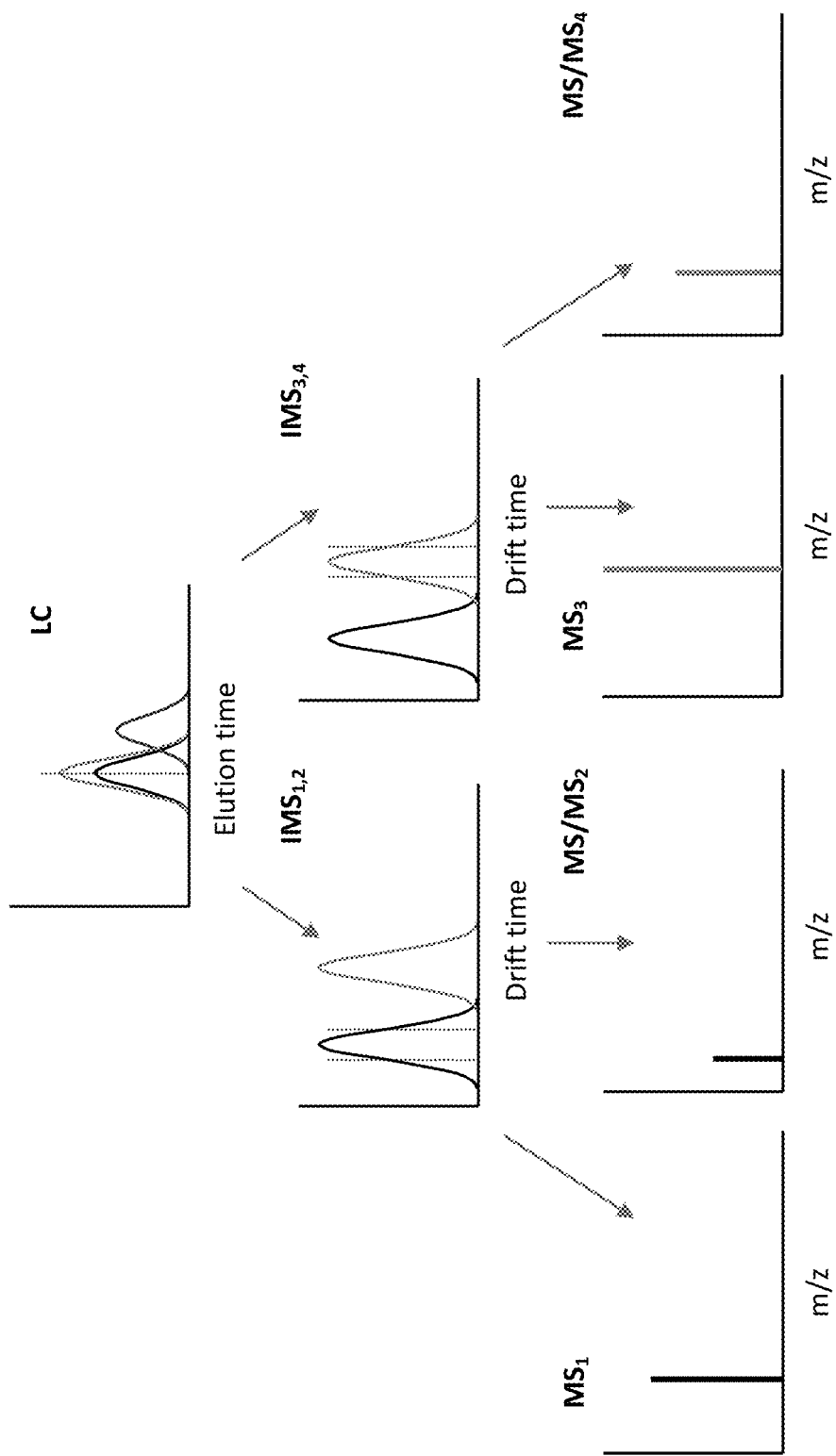
Figure 12C:
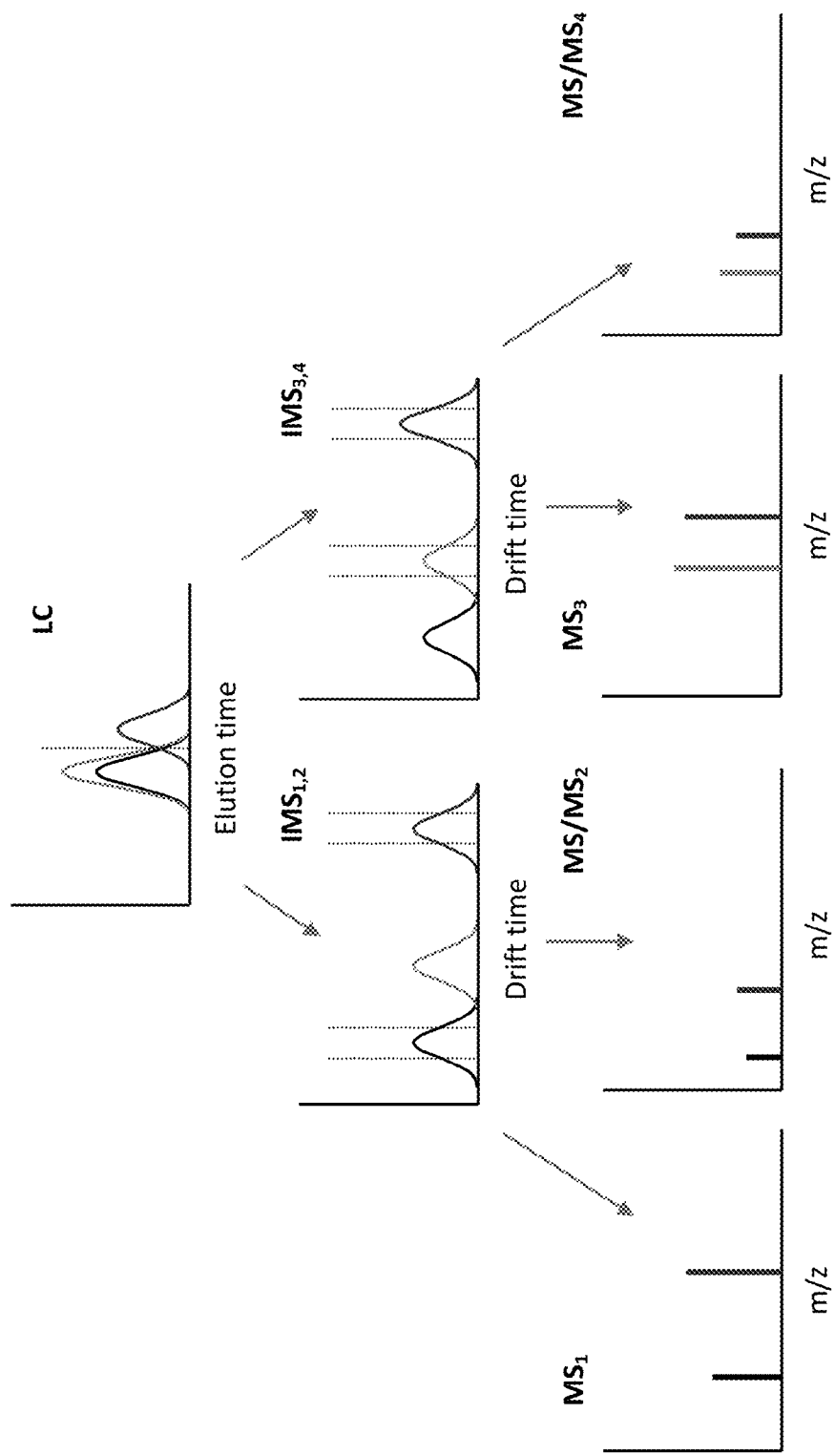
Figure 12D:
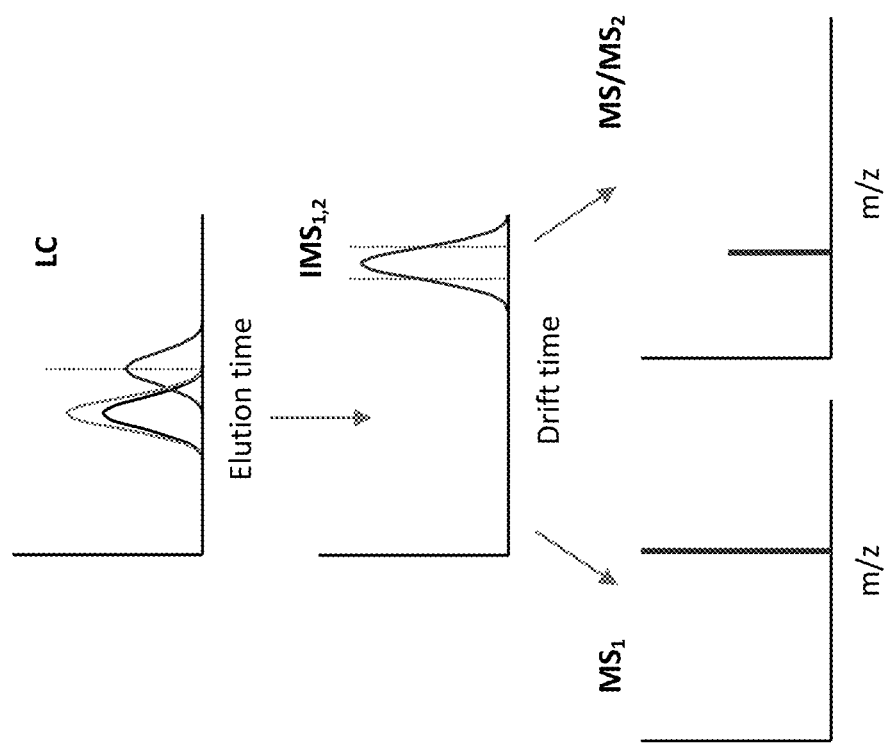

The selection of detected peaks can be performed manually, or under the automated direction of the control software. Once recognition of the peaks has occurred, a custom notched waveform (1004) is generated and applied to the second ion gate. Multiple scan delays are incorporated within this waveform, creating notches; the locations of which are determined by the previously recorded IMS spectrum. The width of each notch can again be either manually selected, or automatically implemented by the software. After a period of time allowing sufficient MS signal averaging to occur, a second notched waveform (1006) is generated and then applied to the second ion gate; the results recorded in a second mass spectrum. An example notch sequence for each pulse is provided in the table in FIG. 10B. For each species that is detected, the ratio of notch widths from waveform 1 and 2 is unique for the passage of a particular ion. In this way, an exclusive fingerprint of ion transmission is characterized when the results of these two mass spectra are combined producing a y axis now expressed as a ratio of ion abundances. For example, only half of the ion intensity for "Peak 5" is transmitted in waveform 1, while all of the intensity is transmitted in waveform 2. This creates an intensity ratio of 1/2 when both mass spectra are compared, as illustrated in FIG. 11. FIG. 11 shows an encoding scheme made possible by ratio comparison of IMS peak area and MS or MS/MS ion intensity due to notch width differences between waveforms for Peak 5. In this case, Waveform 1 selects only half of the area of this particular peak (1101), and Waveform 2 selects all of this peak (1103). Note: MS spectra do not need to be acquired for this method, but are shown to illustrate that precursor intensities (mass spectra 1107 and 1111) are transferred to product ions (mass spectra 1109 and 1113 respectively).

In contrast, the fraction of ion intensity for all of the other peaks gated into the mass spectrometer by waveform 1 and waveform 2 is different, thus resulting in intensity ratios that are distinct and peak specific. Simultaneous ion fragmentation can occur for all types of ions being transferred into the mass spectrometer during each waveform, and the intensities of the product ions will be dictated by the initial abundance of their respective precursor ion. The initial IMS spectrum, along with the choice of notch widths applied to each peak during both waveforms (essentially the area or fraction of ion abundance that is allowed to be detected by MS) are used to calculate the expected intensity ratio for each IMS peak. This facilitates proper identification of every product ion formed, as each fragment detected will be present at one of these expected intensity ratios.

Figure 13A:
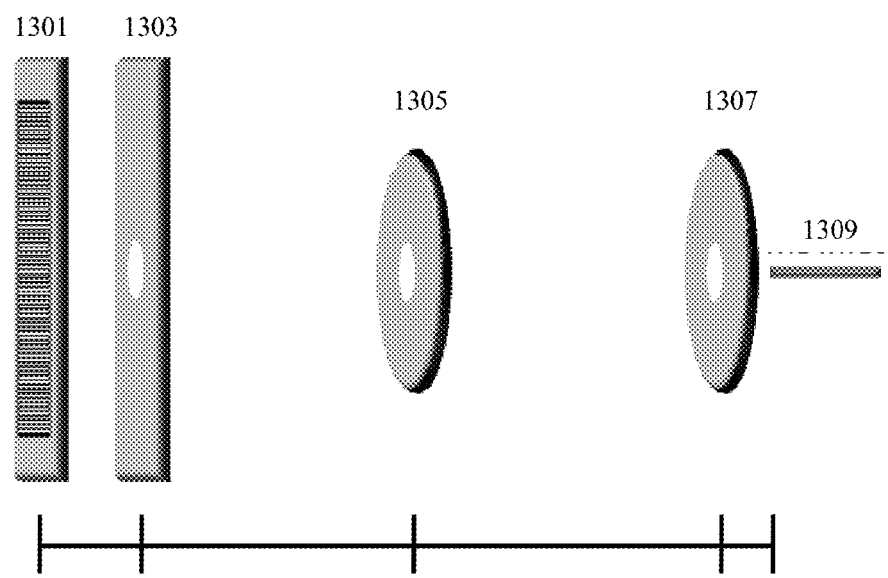
FIGS. 13A and 13B illustrate optimization of the IMS-MS Interface, showing the hardware in FIG. 13A and the resulting spectra in FIG. 13B.
Figure 13B:
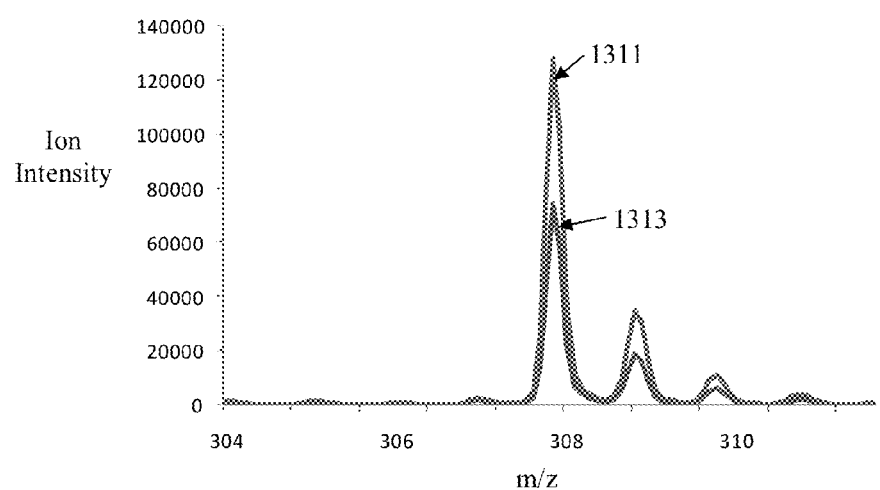

When using a mass spectrometer after an atmospheric-pressure IMS, ion transfer can be maximized by adjusting both the positions and the voltages of a series of lens elements in the mass spectrometer interface region. FIGS. 13A and 13B show one such arrangement for optimization of the IMS-MS interface, with adjustable IMS-MS interface lens elements in terms of both V and relative locations for fine tuning ion transfer into the mass spectrometer (FIG. 13A): the second ion gate 1301 is followed by three lens elements 1303, 1305, and 1307, prior to the mass spectrometer inlet 1309. The resulting changes in ion abundance are shown in FIG. 13B, where the same sample is run under optimized (upper trace 1311) and non-optimized (lower trace 1313) settings.

What is claimed is:

1. A method for operating an ion mobility spectrometer, comprising:
    (a) Opening a first ion gate to allow a packet of mixed ions into the ion mobility analyzer,
    (b) Separating ions in the ion mobility analyzer,
    (c) For each opening of the first gate, opening a second gate multiple times according to a waveform consisting of a series of time windows to allow ions with certain ion mobilities to pass through the second gate and/or to block the ions with other ion mobilities.

2. The method of claim 1, wherein the series of time windows is predetermined by on-line or off-line ion mobility measurement of the mixed ions.

3. The method of claim 1, wherein the series of time windows is predetermined by theoretical calculation of ion mobility of the mixed ions.

4. The method of claim 1, wherein the series of time windows is chosen to select ions with certain collision cross section from the mixed ions.

5. The method of claim 1, wherein the ions with certain ion mobilities are the ions of interest.

6. The method of claim 1, wherein the time windows when the second gate is closed are chosen to selectively block ions with specific ion mobilities.

7. The method of claim 1, further comprising: analyzing the ions that passed through the second gate with a mass spectrometer.

8. The method of claim 1, further comprising:
(a) generating two or more waveforms, wherein the two or more waveforms have different combinations of opening times and widths;
(b) opening and closing the second ion gate according to the first waveform, while collecting a spectrum;
(c) opening and closing the second ion gate according to the second and subsequent waveforms, while collecting additional spectra;
(d) comparing the two or more spectra.

9. The method of claim 8, further comprising:
(a) detecting a first ion mobility spectrum from a sample;
(b) generating two waveforms based on the ion mobility spectrum, wherein the two waveforms have different combinations of notch sizes for each of multiple ion mobility spectrum peaks;
(c) opening and closing the second ion gate according to the first waveform, while collecting fragment ion data from the ions that were allowed through the second ion gate, where the fragment ion data is collected in a mass spectrometer that is downstream of the IMS, and where the mass spectrometer has the ability to fragment ions;
(d) opening and closing the second ion gate according to the second waveform, while collecting fragment ion data in the mass spectrometer;
(e) comparing the two fragment ion mass spectra, and matching each fragment ion with its peak in the first IMS spectrum based on the ratios of the fragment peak intensities detected with the two waveforms, and the notch sizes of the two waveforms.

10. The method of claim 9, wherein the first ion mobility spectrum is detected using a Faraday plate.

11. The method of claim 9, wherein the first ion mobility spectrum is detected using the mass spectrometer.

12. The method of claim 1, wherein the second gate is a segmented ion gate.

13. A ion mobility spectrometer, comprising:
(a) a first ion gate to allow a packet of mixed ions into an ion mobility analyzer to separate ions,
(b) a second gate, and
(c) a controller controlling the gates such that, for each opening of the first gate, the second gate is opened multiple times at a series of time windows to allow ions with certain ion mobilities to pass through the second gate and/or to block the ions with other ion mobilities.

14. The apparatus of claim 13, further comprising a Faraday detector.

15. The apparatus of claim 14, wherein the Faraday detector is a pass-through Faraday detector which allows a portion of the ions to be detected and the remaining portion to pass into a mass spectrometer.

16. The apparatus of claim 15, wherein the Faraday detector is before the second gate.

17. The apparatus of claim 15, wherein the Faraday detector is after the second gate.

18. The apparatus of claim 15, further comprising a mass spectrometer that is behind the second gate and/or the pass-through Faraday detector.

19. The apparatus of claim 18, wherein the second ion gate is the mass spectrometer inlet.

20. The apparatus of claim 13, further comprising a mass spectrometer that is behind the second gate.

21. The apparatus of claim 13, wherein the second gate is a segmented ion gate.

* * * * *